(12) United States Patent
Liu et al.

(10) Patent No.: US 7,473,354 B2
(45) Date of Patent: Jan. 6, 2009

(54) RECYCLED SUPPRESSOR REGENERANTS

(75) Inventors: Yan Liu, Palo Alto, CA (US); Victor Manuel Berber Barreto, Campbell, CA (US); Christopher A. Pohl, Union City, CA (US); John M. Riviello, Santa Cruz, CA (US)

(73) Assignee: Dionex Corporation, Sunnyvale, CA (US)

( * ) Notice: Subject to any disclaimer, the term of this patent is extended or adjusted under 35 U.S.C. 154(b) by 565 days.

(21) Appl. No.: 11/229,022

(22) Filed: Sep. 16, 2005

(65) Prior Publication Data

US 2007/0062873 A1 Mar. 22, 2007

(51) Int. Cl.
    *B01D 15/08* (2006.01)
(52) U.S. Cl. .................. 210/198.2; 210/635; 210/656; 422/70; 205/789
(58) Field of Classification Search ............. 210/635, 210/638, 656, 659, 748, 198.2, 243; 422/70; 205/789.792
    See application file for complete search history.

(56) References Cited

U.S. PATENT DOCUMENTS

| | | | |
|---|---|---|---|
| 3,897,213 A | 7/1975 | Stevens et al. | |
| 3,920,397 A | 11/1975 | Small et al. | |
| 3,925,019 A | 12/1975 | Small et al. | |
| 3,926,559 A | 12/1975 | Stevens | |
| 4,242,097 A * | 12/1980 | Rich et al. | 436/100 |
| 4,455,233 A * | 6/1984 | Pohl et al. | 210/635 |
| 4,615,780 A | 10/1986 | Walker | |
| 4,751,189 A * | 6/1988 | Rocklin | 436/150 |
| 4,999,098 A | 3/1991 | Pohl et al. | |
| 5,248,426 A | 9/1993 | Stillian et al. | |
| 5,352,360 A | 10/1994 | Stillian et al. | |
| 5,433,838 A | 7/1995 | Dasgupta | |
| 5,633,171 A * | 5/1997 | Small et al. | 436/161 |
| 6,325,976 B1 | 12/2001 | Small et al. | |
| 6,425,284 B1 * | 7/2002 | Srinivasan et al. | 73/61.52 |
| 6,436,719 B1 * | 8/2002 | Srinivasan et al. | 436/161 |
| 6,508,985 B2 * | 1/2003 | Small et al. | 422/70 |
| 6,562,628 B1 * | 5/2003 | Liu et al. | 436/161 |
| 6,682,701 B1 * | 1/2004 | Liu et al. | 422/99 |
| 7,329,346 B2 * | 2/2008 | Liu et al. | 210/198.2 |
| 7,402,283 B2 * | 7/2008 | Liu et al. | 422/70 |

FOREIGN PATENT DOCUMENTS

EP 0180321 A2 5/1986
WO WO02/04940 A1 1/2002

OTHER PUBLICATIONS

P.R. Haddad et al., *J. Chromatogr.* A 1000 (2003) 725-742 (Developments in suppressor technology for inorganic ion analysis by ion chromatography using conductivity detection).

* cited by examiner

*Primary Examiner*—Ernest G Therkorn
(74) *Attorney, Agent, or Firm*—Morgan, Lewis & Bockius LLP; David J. Brezner

(57) ABSTRACT

A suppressed ion chromatographic apparatus using a regenerant recycle loop, comprising (a) an ion separation device, (b) a membrane suppressor, (c) a detector, (d) a container for regenerant solution, (e) a first conduit between the ion separation device and the suppressor, (f) a second conduit between the regenerant solution container and the suppressor, (g) a third conduit between the suppressor and the regenerant solution container, and (h) a regenerant solution recycle loop out of fluid communication with the detector outlet.

11 Claims, 9 Drawing Sheets

RECYCLED SUPPRESSOR REGENERANTS

BACKGROUND OF THE INVENTION

The present invention relates to ion chromatography systems for determination of both anionic and cationic analytes.

Ion chromatography is a widely used analytical technique for the determination of anionic and cationic analytes in various sample matrices. Ion chromatography, also called suppressed ion chromatography, includes a chromatographic separation stage using an eluent containing an electrolyte, an eluent suppression stage, followed by the detection stage, typically using an electrical conductivity detector. In the chromatographic separation stage, ionic analytes of an injected sample are eluted through a separation column and separated from each other using an electrolyte as the eluent. In the suppression stage, an eluent suppression device, or suppressor, is the critical system component used to convert the eluent into a weakly conducting form and enhance the conductance of target analytes. This technique has been described in detail in U.S. Pat. Nos. 3,897,213, 3,920,397, 3,925,019, and 3,926,559.

Even though ion chromatography today comprises a number of separation and detection modes, ion chromatography with suppressed conductivity detection remains the most widely practiced form of the technique. The original suppressors were columns packed with ion-exchange resins in appropriate ionic forms. Those packed-bed suppressors had a relatively large dead volume and required frequent off-line chemical regeneration. To overcome this problem, suppressors based on ion-exchange fibers and membranes were developed. Over the years, several designs of electrolytically-regenerated membrane suppressors as described in U.S. Pat. Nos. 4,999,098, 5,248,426, 5,352,360, and 6,325,976 have been also developed to overcome the limitations associated with the chemically-regenerated membrane suppressors. The electrolytic suppressors offer several advantages in ion chromatography. They provide continuous and simultaneous suppression of eluents, regeneration of the suppression bed, and sufficient suppression capacity for all common IC applications. They are easy to operate because either the suppressed eluent or water is used to create regenerant ions electrolytically, and there is no need to prepare regenerant solutions off-line. They are compatible with gradient separations. They have very low suppression zone volume, which makes it possible to achieve separations with very high chromatographic efficiency.

In the operation of electrolytically-regenerated membrane suppressors, it is sometimes preferred to operate the electrolytic membrane suppressors in the external water mode because the type of detector used is not amenable to the recycle mode of operation or because lower suppressed background noise achievable in the external water mode of operation is desirable. The external water regenerant is typically operated at flow rates that are 2 to 10 times higher than the eluent flow rate and thus typically consume a significant amount of water regenerant. For example, a total of 2628 liters of water is required if an ion chromatography system is operated continuously at a separation flow rate of 1.0 mL/min and the water regenerant is operated at 5 mL/min and 24 hours per day for 365 day per year. When a constant supply of large amounts of high purity water from an external source is required for continuous operation, the IC system operators face the waste disposal and other logistical challenges to system operation.

Even though the use of chemically-regenerated membrane suppressors have decreased somewhat in recent years, the membrane suppressors offer the benefits of long lifetime, low noise, and better compatibility with applications where organic solvents are used as in the eluents. In the operation of chemically-regenerated membrane suppressors, an external source of either acid or base regenerant solution is required to generate the suppressor continuously. The external acid or base regenerant is typically operated at flow rates that are 2 to 10 times higher than the eluent flow rate and thus typically consume a significant amount of regenerants. The consistent preparation of such large amount of the regenerant as well as the disposal of the used regenerant can pose serious logistical challenges to the system operators in terms of costs and labor, especially in cases where unattended or less frequently attended operations are required.

There is a need to minimize waste disposal, and reduce operating costs of the regenerant solutions used in the operation of both the chemically-regenerated and electrolytically-regenerated suppressors.

SUMMARY OF THE INVENTION

In one embodiment, the invention is a suppressed ion chromatographic apparatus using a regenerant recycle loop, comprising (a) an ion separation device including ion separation medium with exchangeable ions of one charge, positive or negative, (b) a membrane suppressor comprising a sample stream flow channel, having an inlet and an outlet, a regenerant flow channel, having an inlet and an outlet, and an ion exchange membrane separating the sample stream flow channel and regenerant flow channel, (c) a detector having an inlet and an outlet, the detector inlet being in fluid communication with the sample stream flow channel outlet, (d) a container for regenerant solution, (e) a first conduit providing fluid communication between the ion separation device and the sample stream flow channel inlet, (f) a second conduit providing fluid communication between the regenerant solution container and the regenerant flow channel, (g) a third conduit providing fluid communication between the regenerant channel and the regenerant solution container, and (h) a regenerant solution recycle loop comprising the second and third conduits, the recycle loop being out of fluid communication with the detector outlet.

In another embodiment, the invention is a method for suppressed ion chromatography using a regenerant solution recycle loop, comprising (a) separating sample ions of one charge, positive or negative, in a liquid sample stream including eluent by flowing the same through ion separation medium in an ion separation device, (b) suppressing the eluent by flowing the effluent from the ion separation medium through a sample stream flow channel of a membrane suppressor comprising a sample stream flow channel, having an inlet and an outlet, a regenerant flow channel, having an inlet and an outlet, and an ion exchange membrane separating the sample stream flow channel and regenerant flow channel, (c) detecting the separated sample ions by flowing the effluent from the sample stream flow channel through a detector, (d) flowing a regenerant solution through the regenerant flow channel, (e) providing a regenerant solution reservoir, and (f)

flowing the regenerant solution between the regenerant solution reservoir and the regenerant flow channel in a recycle loop independent of liquid flow through the detector.

DETAILED DESCRIPTION OF THE INVENTION

The present invention relates to various modes of recycling either (1) the regenerants such as water used in the operation of the electrolytically-regenerated suppressors when they are operated in the external water mode, or (2) acid or base regenerants used in the operation of chemically-regenerated suppressors.

Figure 1:
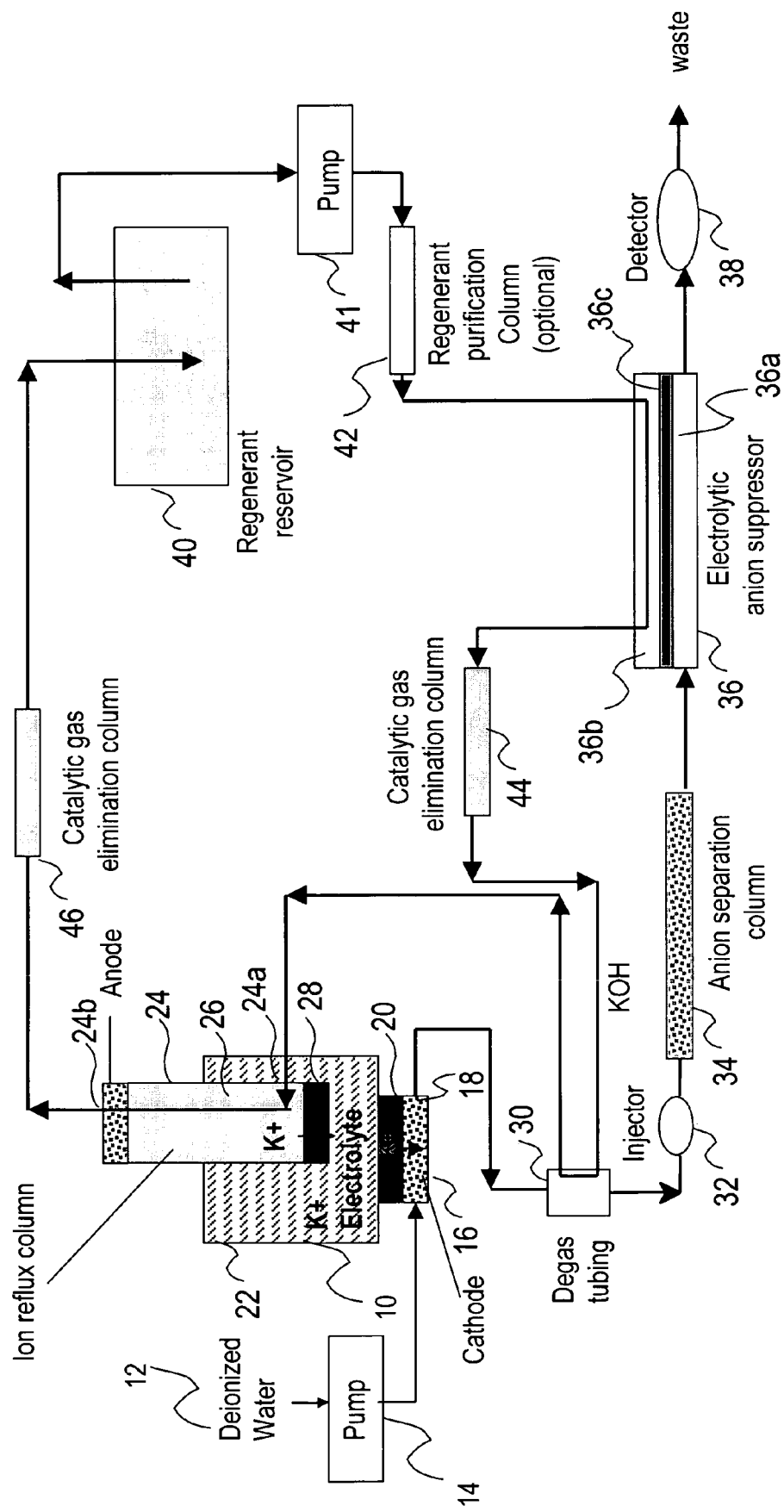
FIGS. 1-6 are schematic representations of different suppressed ion chromatography systems with recycled eluents according to the present invention.

Referring to FIG. 1, the invention will first be described in the recycled water mode used in the operation of the electrolytically-regenerated suppressors when they are operated in the external water mode. FIG. 1 illustrates the basic components of one of the preferred embodiments of ion chromatography system using recycled suppressor regenerant water. In this embodiment, an eluent generator 10 of the type illustrated in FIG. 1 of U.S. Pat. No. 6,682,701 is used with some modification as described below. Other eluent generators such as illustrated in the '701 patent can be used in combination with the ion chromatography system of the present invention. The principles of operation of the electrolytic eluent generator are fully described in U.S. Pat. No. 6,682,701.

Other electrolytic eluent generators may be used such as ones which generate a carbonate salt such as potassium carbonate illustrated in PCT Application WO/2004/024302. In this instance, the ion chromatography system downstream from the eluent generator also is as illustrated in FIG. 1. Other eluent generators can be used, e.g. as illustrated in U.S. Pat. No. 5,045,204 or U.S. Pat. No. 6,562,628. Although the eluent generators are illustrated for anion analysis and the generation of cations such as potassium ions, for cation analysis, the same system may be used for generating MSA or other anions for an acid eluent by appropriate reversal of the polarity of the membrane ion exchange resin and electrodes such as illustrated in U.S. Pat. No. 6,682,701.

Referring specifically to the embodiment of FIG. 1, illustrated for the analyses of anions, deionized water 12 from a source, not shown, is pumped under pressure supplied by pump 14, through the high pressure base generation chamber 16 of electrolytic generator 10. As illustrated, chamber 16 includes a cathode 18 in communication with a cation exchange bed. The high pressure base generation chamber is separated by a cation exchange connector 20 from a low pressure ion source reservoir 22 containing a source of eluent ion. As illustrated, the system is for anion analysis in which the ions to be supplied for the anion analyte are cations, potassium ion as illustrated, or sodium, lithium or other cations. The ion source reservoir may be in the form of a base or salt solution which can be replenished as illustrated in the '701 patent. The charged perm selective membrane barrier or connector 20 substantially prevents bulk liquid flow while providing an ion transport bridge to transport the potassium ions into the base generation chamber. Suitable membranes, e.g. ones formed of Nafion®, are illustrated in the '701 patent.

The ion source reservoir 22 of the embodiment shown in FIG. 1 also contains an ion reflux column 24 that has a fluid inlet port 24a and a fluid outlet port 24b. The ion reflux column 24 is packed with cation exchange resin in a bed 26 and preferably is predominantly in the hydronium form. Outlet 24b is fitted with a flow-through Pt anode which is in direct physical contact with the cation exchange resin bed 26. The inlet region of the column is fitted with cation exchange connector 28 that separates resin bed 26 from the potassium electrolyte solution in the ion source reservoir 22. The charged permselective membrane barrier or connector 28 substantially prevents bulk liquid flow while providing an ion transport bridge to transport the potassium ions from the cation exchange resin bed 26 in the ion reflux column 24 into the ion source reservoir 22.

In the embodiment illustrated in FIG. 1, electrolysis is performed to provide the reaction illustrated in the '701 patent so that the base, KOH, is generated in base generation chamber 16. Under the applied electric field, the potassium ions migrate from the ion source reservoir 22 across the ion exchange connector 20 to combine with hydroxide ions generated at the cathode 18 to form a KOH eluent. The concentration of KOH solution formed is proportional to the applied current and inversely proportional to the flow rate of the deionized water carrier stream.

Hydrogen gas is generated at cathode 18 which could interfere with analysis of the sample. Thus, it is preferable to use a degassing tubing device 30 typically using a porous membrane adjacent to flow to remove the hydrogen gas from the sample stream, also illustrated in the '701 patent.

Sample is injected at sample injector 32 and carried by the eluent from the KOH generation chamber 16 to ion exchange chromatographic separation column 34. For anion analysis, separation is performed using anion separation medium, typically a packed bed of ion exchange resin in the column. As illustrated in FIG. 1, the effluent from the anion separation column flows to an electrolytic anion suppressor 36 and a conductivity detector 38, although other detectors such as UV-Vis, electrochemical, and mass spectrometry detectors may be used.

In the embodiment illustrated in FIG. 1, the electrolytic anion suppressor is operated in the external water mode (i.e., an external source of water is used in the electrolytic generation of regenerant hydronium ions). The electrolytic anion suppressor used in this embodiment can be of the type of the electrolytically-regenerated membrane suppressors as described in U.S. Pat. Nos. 4,999,098, 5,248,426, 5,352,360, and 6,325,976 or other types. The principles of operation of electrolytically-regenerated membrane suppressors are described in details in those patents. As illustrated, suppressor 36 is a flat membrane suppressor which includes a sample stream flow channel 36a, a regenerant flow channel 36b, and a permselective ion exchange membrane 36c separating the two channels.

Referring to the embodiment of FIG. 1, the regenerant water in a container or reservoir 40 is pumped by pump 41 through optional regenerant purification column 42 that is packed with anion exchange resin. This column is used to remove dissolved carbon dioxide and other anionic contaminants such as carbonate in the regenerant water. Column 42 may also contain a zone of cation exchange resin to remove cationic contaminants and a zone of appropriate chromatographic packing material to remove neutral contaminants in the regenerant water. The regenerant water leaving column 42 then flows into regenerant flow channel 36b of the electrolytic suppressor 36. The solution flowing out the regenerant flow channel 36b contains a mixture of KOH solution and stoichiometrical amounts of hydrogen gas and oxygen gas formed through the oxidation and reduction of water at the anode ($H_2O-2e^- \rightarrow 2H^+ + \frac{1}{2}O_2 \uparrow$) and cathode ($2H_2O+2e^- \rightarrow 2OH^- + H_2 \uparrow$) during the operation of the anion electrolytic suppressor. This suppressor regenerant effluent mixture is passed through optional catalytic gas elimination column 44 where hydrogen and oxygen react catalytically to form water as described in U.S. patent application Ser. No. 11/065,335, filed Feb. 23, 2005, entitled "Ion Chromatography System Using Catalytic Gas Elimination". The use of column 44 offers the benefits of eliminating hydrogen and oxygen gases and the generation of water for the regenerant solution.

The KOH solution leaving column 44 is free of hydrogen and oxygen gas. This solution may then be passed though the low pressure chamber of degas tubing assembly 32 to remove hydrogen gas formed in the electrolytic generation of the KOH eluent in chamber 16. The mixture of KOH and hydrogen is then directed to the inlet of the ion reflux column 24. Under the applied electrical field, potassium ions migrate across the cation exchange connector 28 located near the inlet region of column 24 into the potassium ion source reservoir 22. The amount of potassium ions migrating into the potassium ion source reservoir 22 is equal to the amount of potassium ions migrating out of reservoir 22 into the KOH generation chamber 16 in the electrolytic generation of KOH eluent. Thus, the ion chromatography system illustrated in FIG. 1 utilizes a perpetual process of consuming and recycling of potassium source ions in ion chromatographic process. Perpetual process of consuming and recycling of potassium source ions has been described in U.S. Pat. No. 6,562,628.

Since potassium ions are recycled back to the ion source reservoir 22, the effluent leaving the outlet of ion reflux column 24 contains water and stoichiometric amount of hydrogen gas and oxygen gas. The effluent from column 24 can be then passed through another optional catalytic gas elimination column 46 where hydrogen and oxygen react catalytically to form water. The water leaving column 46 is then recycled back to the water regenerant reservoir 40. Therefore, the ion chromatography system illustrated in FIG. 1 provides a novel approach to recycle the regenerant water used in the operation of an anion electrolytic suppressor 36.

The regenerant solution recycles through the ion chromatography system out of fluid communication with the sample stream exiting from the detector.

Figure 2:
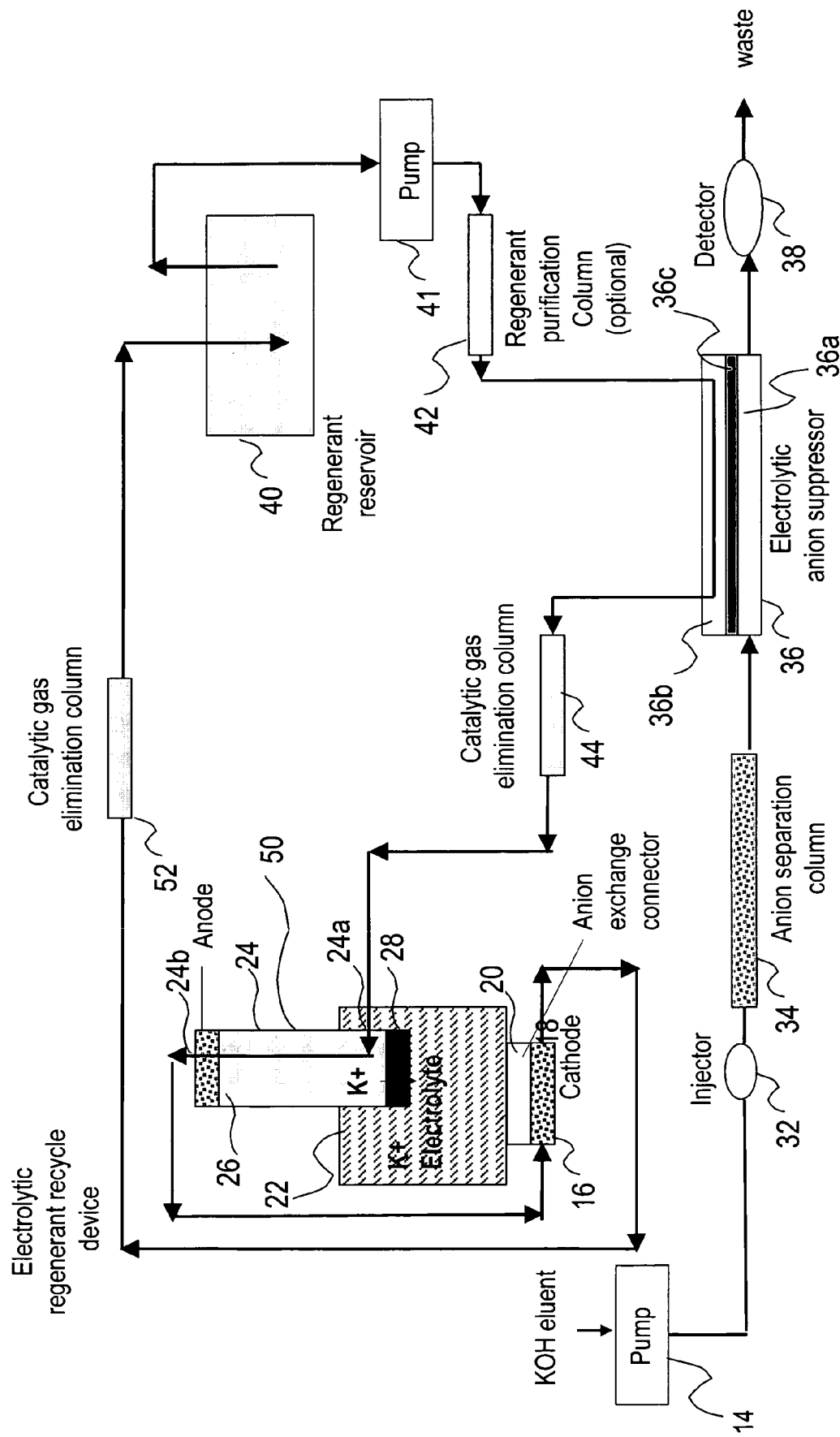

FIG. 2 shows another embodiment of the present invention. Like parts in FIGS. 1 and 2 will be designated with like numbers. In this embodiment, the eluent used in the ion chromatographic process can be prepared by conventional means off-line or generated electrolytically on-line. Sample is injected in injector 32 and carried by the eluent pumped by pump 14 from a source, not shown, to an ion exchange chromatographic separation column 34. For anion analysis, separation is performed using anion exchange separation medium. As illustrated, the effluent from column 34 flows to an electrolytic anion suppressor 36 and detector 38.

In the embodiment illustrated in FIG. 2, electrolytic anion suppressor 36 is operated in the external water mode. The regenerant water is pumped by pump 41 from reservoir 40 through a regenerant purification column 42 used to remove ionic and neutral contaminants in the regenerant water. The regenerant water leaving the regenerant purification column 42 then flows into the regenerant flow channel 36b of electrolytic suppressor 36. The solution flowing out the regenerant flow channel 36b contains a mixture of KOH solution and stoichiometrical amounts of hydrogen gas and oxygen gas formed through the oxidation and reduction of water at the anode ($H_2O-2e^- \rightarrow 2H^+ + \frac{1}{2}O_2\uparrow$) and cathode ($2 H_2O+2e^- \rightarrow 2OH^{31} +H_2\uparrow$) during the operation of the anion electrolytic suppressor. This suppressor regenerant effluent mixture is passed through optional catalytic gas elimination column 44 where hydrogen and oxygen react catalytically to form water as described above for the embodiment shown in FIG. 1.

The KOH solution leaving catalytic gas elimination column 44 is free of hydrogen and oxygen gas and is directed to the inlet of the ion reflux column 24 in the electrolytic regenerant recycle device 50. Under the applied electrical field, potassium ions migrate across the cation exchange connector 28 into the electrolyte reservoir 22. In the meantime, water is oxidized to form hydronium ions and oxygen gas at the anode located in the outlet 24b of device 50. Hydronium ions migrate into the resin bed 26 to replenish the hydronium ions consumed due to the neutralization reaction with the incoming hydroxide ions. Since potassium ions are removed into the electrolyte reservoir 22, the ion reflux column effluent contains water and oxygen gas generated at the device anode and is directed to flow through the cathode compartment 16 which is connected to the electrolyte reservoir 22 through an anion exchange connector 20. Under the applied electrical field, hydroxide ions formed from the reduction of water migrate across the anion exchange connector 20 into the electrolyte reservoir 22 to maintain the solution charge neutrality in the solution reservoir. In this embodiment, the amount of current applied to the electrolytic regenerant recycle device 50 should be adjusted to a level that is sufficient to ensure the complete removal of KOH in the regenerant stream.

The effluent leaving the outlet of the cathode compartment 16 of the electrolytic regenerant recycle device 50 contains water and stoichiometric amount of hydrogen gas and oxygen gas. This effluent can be then passed through another catalytic gas elimination column 52 where hydrogen and oxygen react catalytically to form water. The water leaving the catalytic gas elimination column 46 is then recycled back to the water regenerant reservoir 40. The ion chromatography system illustrated in FIG. 2 provides another approach according to the invention to recycle the regenerant water used in the operation of an anion electrolytic suppressor. In contrast to the embodiment shown in FIG. 1, the embodiment illustrated in FIG. 2 allows the use of the eluent that is either prepared by conventional means off-line or generated electrolytically on-line.

Figure 3:
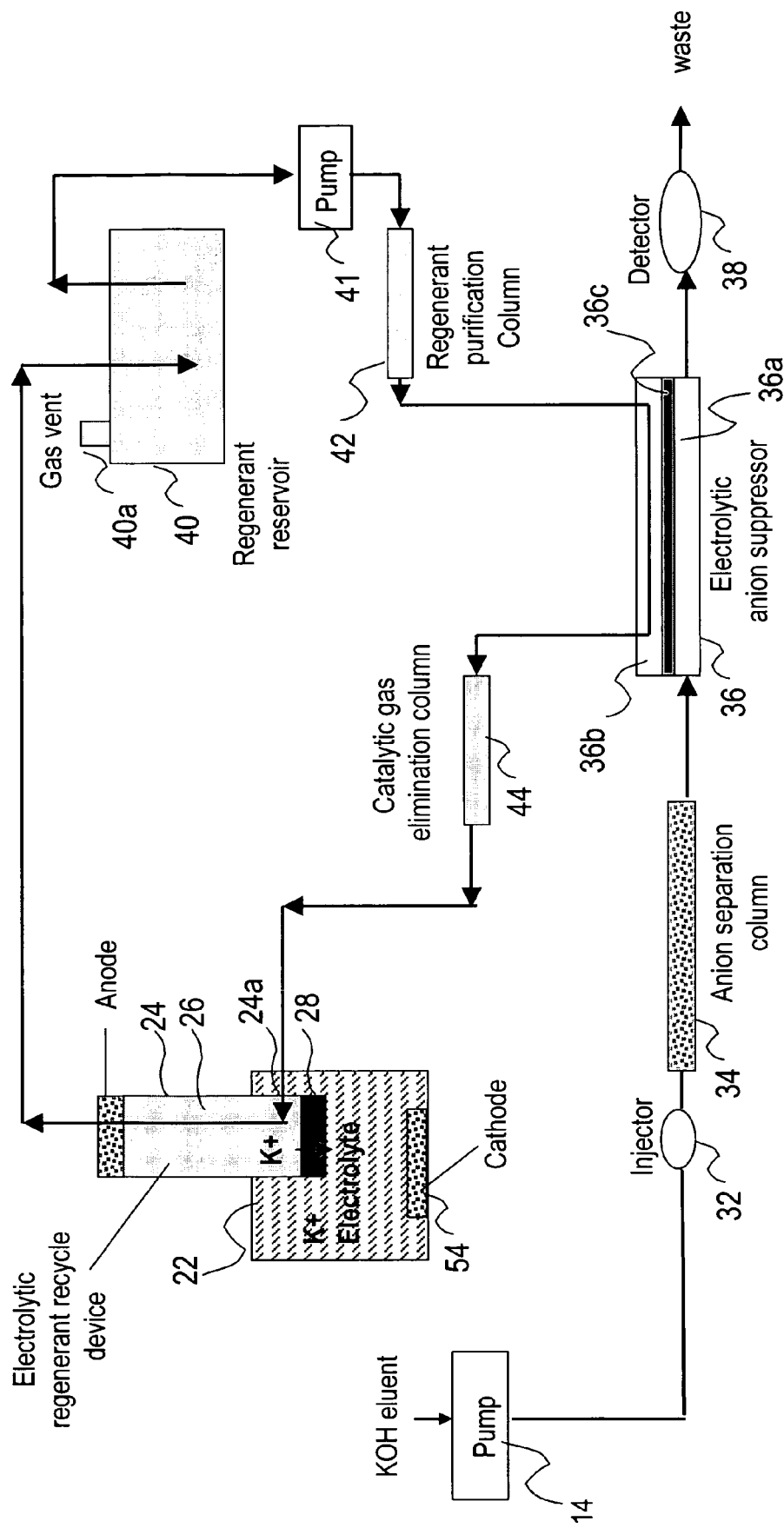

FIG. 3 shows another embodiment of the present invention. In this embodiment, the eluent used in the ion chromatographic process can be prepared by conventional means off-line or generated electrolytically on-line. The ion chromatographic process is performed in this embodiment using the similar components described previously for the embodiment shown In FIG. 2. Like parts with FIGS. 1 and 2 will be illustrated with like numbers. In the embodiment illustrated in FIG. 3, the electrolytic anion suppressor 36 also is operated in the external water mode. The regenerant water from reservoir 40 is pumped through optional regenerant purification column 42 used to remove ionic and neutral contaminants in the regenerant water. This suppressor regenerant effluent mixture from regenerant channel 36b is passed through a catalytic gas elimination column 44 where hydrogen and oxygen react catalytically to form water as described previously. The KOH solution leaving the catalytic gas elimination column 44 is free of hydrogen and oxygen gas and is directed to the inlet of the ion reflux column 24 in the electrolytic regenerant recycle device 50.

The electrolytic regenerant recycle device in the embodiment shown in FIG. 3 is constructed such that the device cathode 54 is placed directly in the electrolyte reservoir. Under the applied electrical field, potassium ions migrate across the cation exchange connector 28 located near the inlet region of the ion reflux column into the electrolyte reservoir. Water is oxidized to form hydronium ions and oxygen gas at the anode located in the outlet 24b of ion reflux column. Hydronium ions migrate into the resin bed 26 to replenish the hydronium ions consumed due to the neutralization reaction with the incoming hydroxide ions. In the meantime, hydroxide ions are formed from the reduction of water at cathode 54 to maintain the solution charge neutrality in the electrolyte reservoir 22. In this embodiment, the amount of current applied to the electrolytic regenerant recycle device 50 preferably is adjusted to a level that is sufficient to ensure the complete removal of KOH in the regenerant stream.

In the embodiment shown in FIG. 3, effluent from ion reflux column 24 contains water and oxygen gas generated at the device anode and is recycled back into the water regenerant reservoir 40 which is fitted with a vent port 40a to allow the release of oxygen gas into the ambient. In this embodiment, there is a consumption of water due to the oxidation reaction at the anode of the ion reflux column 24. The amount of water consumed is determined by the amount of current applied to device 50 and is rather minute under the typical ion chromatographic operating conditions. Therefore, the ion chromatography system illustrated in FIG. 3 provides another approach according to the invention to recycle the regenerant water used in the operation of an anion electrolytic suppressor.

Figure 4:
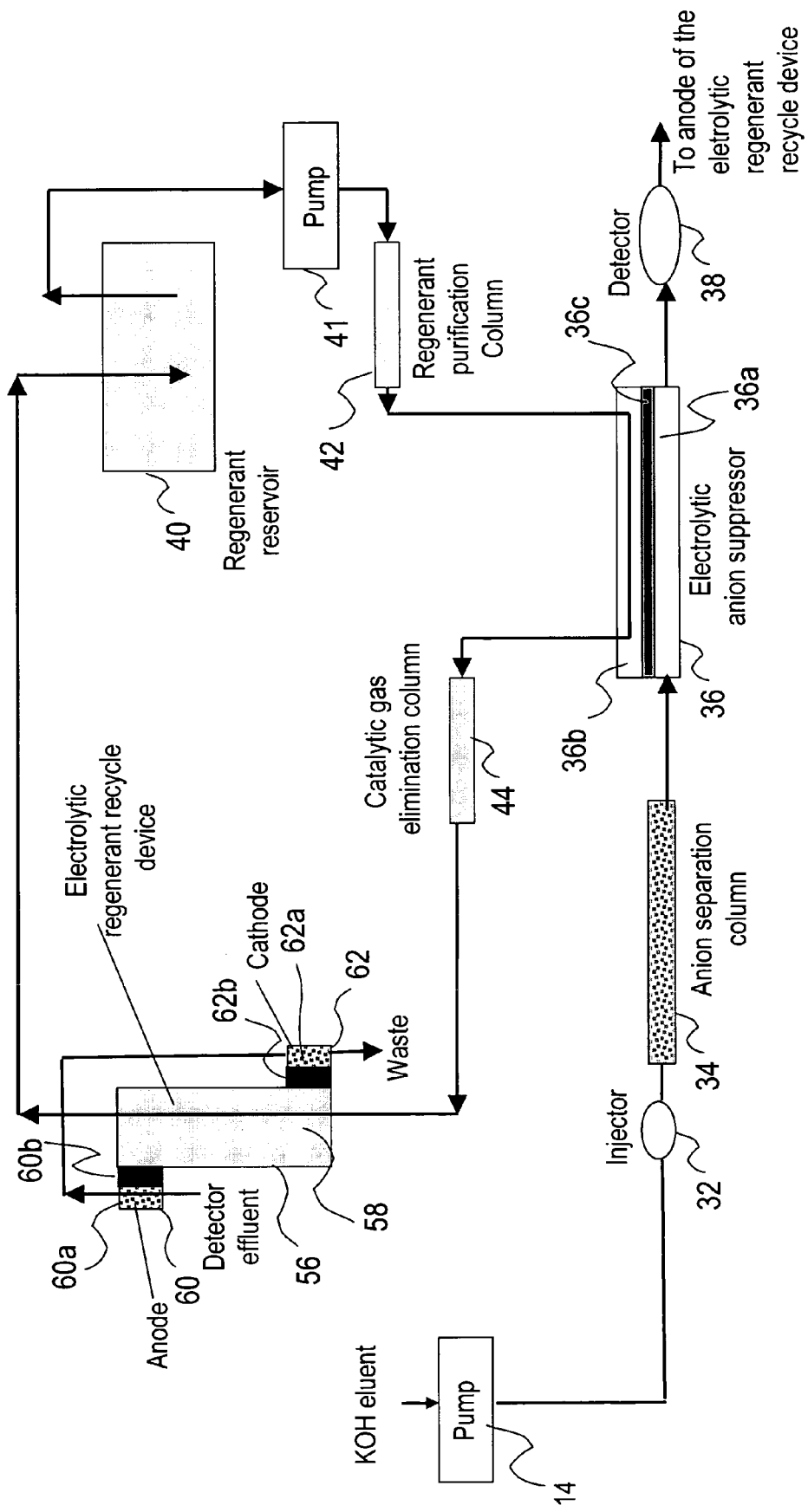

FIG. 4 illustrates another embodiment of ion chromatography systems in which the suppressor regenerant water is recycled in the operation of the electrolytically-regenerated suppressor operated in the external water mode. Like parts with those of FIGS. 1-3 will be designated with like numbers. In this embodiment, the eluent used in the ion chromatographic process can be prepared by conventional means off-line or generated electrolytically on-line. The ion chromatographic process is performed in this embodiment using the similar components described previously. The regenerant solution from reservoir 40 is pumped by pump 41 through a regenerant purification column 42 used to remove anionic and neutral contaminants in the regenerant water. This suppressor regenerant effluent mixture is passed through a catalytic gas elimination column 44 where hydrogen and oxygen react catalytically to form water as described previously. The KOH solution leaving the catalytic gas elimination column 44 is free of hydrogen and oxygen gas and directed into the inlet of an electrolytic regenerant recycle device 56.

In the embodiment shown in FIG. 4, the electrolytic regenerant recycle device may take the form of a column 58 packed with a cation ion exchange resin bed. The resin is suitably contained in the column by porous frits at the column inlet and outlet. The device is fitted with an anode compartment 60 near the outlet region of the cation exchange resin bed and a cathode compartment near the inlet region of the cation exchange resin bed. The anode and cathode compartments have inlet and outlet liquid connecting ports. Electrodes 60a and 62a in the anode and cathode compartments, respectively, are preferably separated from the resin bed by cation exchange connectors 60b and 62b, respectively, that prevent any significant liquid flow but permit the transport of ions only of the same charge as the charge of exchangeable ions on resin bed. Overall, the construction and operation of this embodiment of electrolytic regenerant recycle device is similar to the continuously regenerated packed bed suppressor described in FIG. 2 of U.S. Pat. No. 6,325,976. The electrolytic regenerant recycle device serves the function of electrolytically suppressing the KOH solution coming from the catalytic gas elimination column 44. In this embodiment, the amount of current applied to the electrolytic regenerant recycle device should be adjusted to a level that is sufficient to ensure the complete removal of KOH in the regenerant stream.

In the embodiment shown in FIG. 4, the detector effluent may be directed to flow through the anode and cathode compartments 60 and 62 of the electrolytic regenerant recycle device as illustrated in U.S. Pat. No. 6,325,976. This flowing liquid stream carries the KOH out of the cathode compartment to waste. The suppressed effluent from the electrolytic regenerant recycle device is water and thus can be recycled back into the regenerant water reservoir. Therefore, the ion chromatography system illustrated in FIG. 4 provides another novel approach to recycling the regenerant water used in the operation of an anion electrolytic suppressor.

In another embodiment, not shown, the effluent from cathode chamber 62, which comprises an KOH solution may be cycled to injector 32 as a source of part or all of the eluent, thereby reducing or eliminating the external KOH source. Such recycle is illustrated in U.S. Pat. No. 6,027,643.

Figure 5:
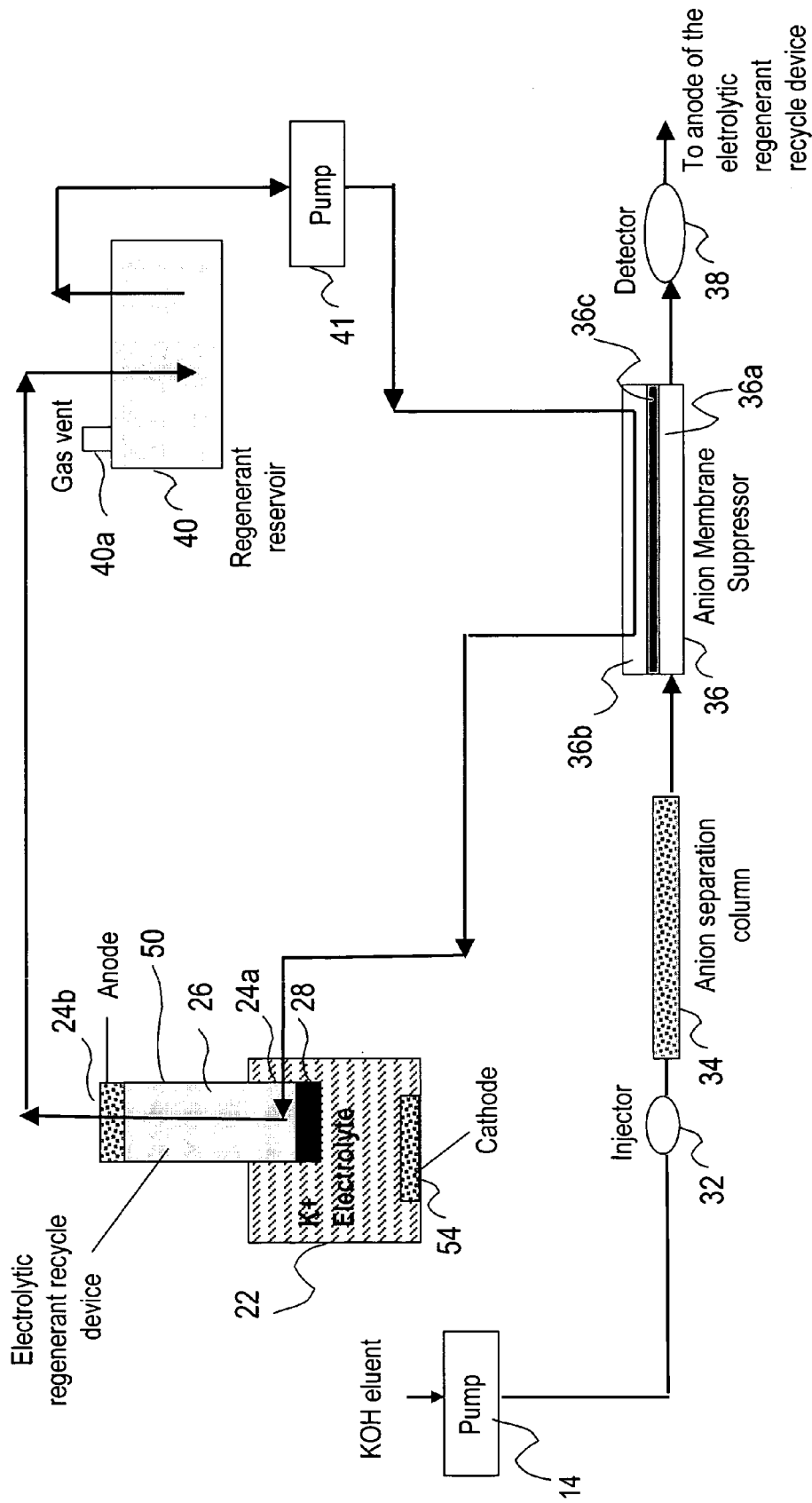

The present invention is also applicable to the recycle of acid or base regenerants used in the operation of chemically-regenerated suppressors in ion chromatography systems. FIG. 5 illustrates one embodiment of ion chromatography systems in which sulfuric acid regenerant used in the operation of an anion membrane suppressor is recycled. Like parts with the embodiments of FIGS. 1-4 will be designated with like numbers. In this embodiment, the eluent used in the ion chromatographic process can be prepared by conventional means off-line or generated electrolytically on-line. The ion chromatographic process is performed using similar components described previously, except that a chemically-regenerated membrane system suitably of the type described in FIG. 1 of U.S. Pat. No. 4,999,098, is used. In the embodiment illustrated in FIG. 5 herein, the sulfuric acid regenerant is delivered by a pump 41 from the regenerant reservoir 40 into the suppressor regeneration flow channel 36b to supply hydronium ions used in the suppression of the KOH eluent. The effluent from regeneration flow channel 36b contains a mixture of potassium sulfate and sulfuric acid. The used regenerant liquid stream is then directed to the inlet 24a of the ion reflux column 24 in the electrolytic regenerant recycle device 50.

The construction and operation of the electrolytic regenerant recycle device of the embodiment illustrated in FIG. 5 is similar to the one used in the embodiment illustrated in FIG. 3. Under the applied electrical field, potassium ions in the regenerant stream migrate across the cation exchange connector 28 located near the inlet region of the ion reflux column 24 into the electrolyte reservoir 22. Water is oxidized to form hydronium ions and oxygen gas at the anode located in the outlet 24b of ion reflux column. Hydronium ions combine with the incoming sulfate ions to form sulfuric acid. In the meantime, hydroxide ions formed from the reduction of water at the cathode 54 combine with potassium ions to maintain the solution charge neutrality in the electrolyte reservoir. In this embodiment, the amount of current applied to the electrolytic regenerant recycle device 50 should be adjusted to a level that is sufficient to ensure the complete removal of potassium ions in the regenerant stream to convert potassium sulfate to sulfuric acid.

In the embodiment shown in FIG. 5, the ion reflux column 24 effluent contains the sulfuric acid regenerant and oxygen gas generated at the device anode and is directed to recycled back to the sulfuric acid regenerant reservoir 40 which is fitted with a vent port (not shown) to allow the release of oxygen gas into the ambient. In this embodiment, there is a consumption of water due to the oxidation reaction at the anode of the electrolytic regenerant recycle device 50. The amount of water consumed is determined by the amount of current applied to the electrolytic regenerant recycle device 50 and rather minute under the typical ion chromatographic operating conditions. Therefore, the ion chromatography system illustrated in FIG. 5 provides a novel approach to recycle the sulfuric acid regenerant used in the operation of the chemically-regenerated suppressor in an ion chromatography system.

Figure 6:
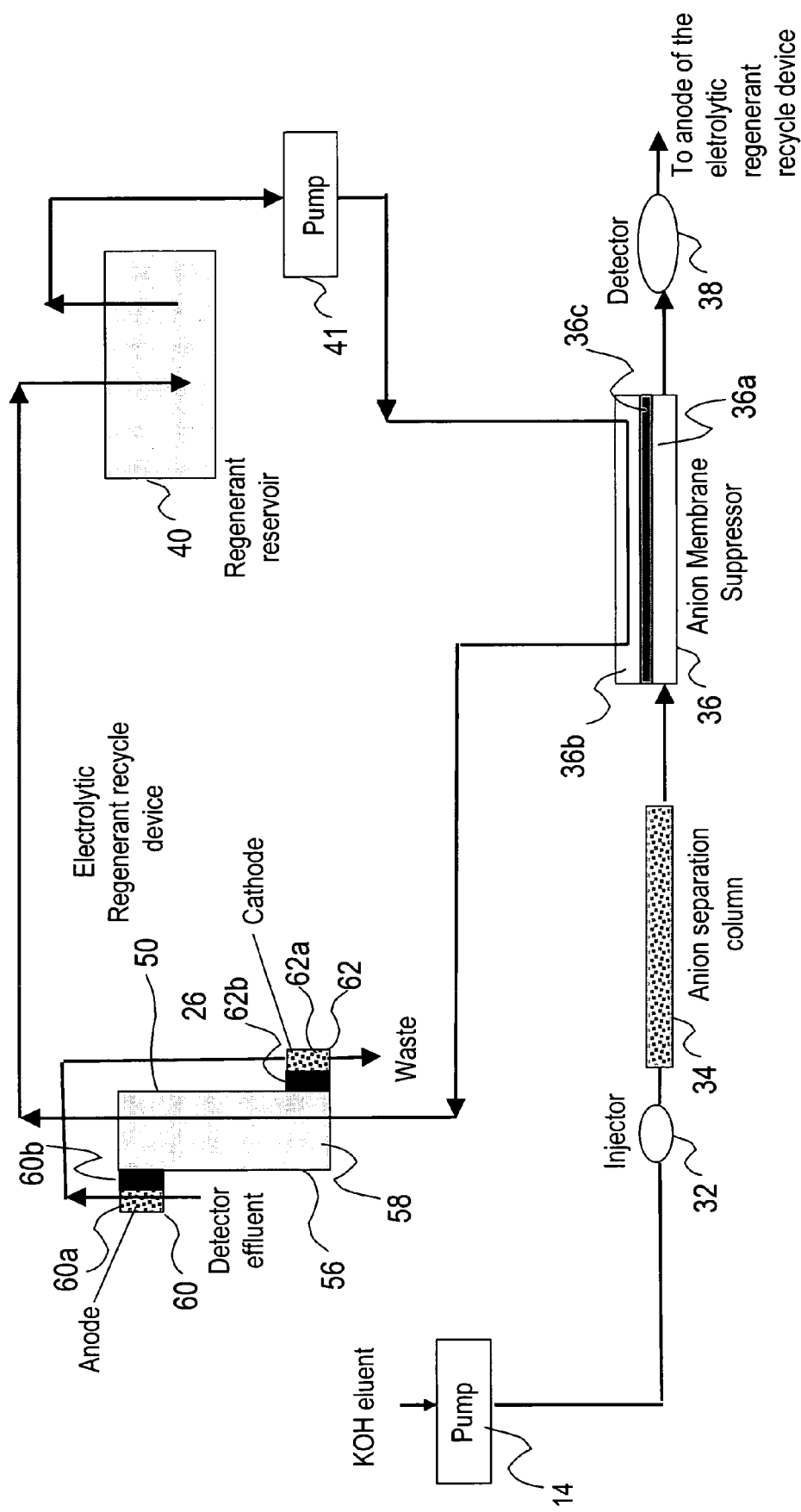

FIG. 6 illustrates another preferred embodiment of ion chromatography systems in which the sulfuric acid regenerant used in the operation of an anion membrane suppressor is recycled. In this embodiment, the eluent used in the ion chromatographic process can be prepared by conventional means off-line or generated electrolytically on-line. The ion chromatographic process is performed using similar components described previously, except that a chemically-regenerated membrane suppressor system, suitably of the type described in FIG. 1 of U.S. Pat. No. 4,999,098, is used. In the embodiment illustrated in FIG. 6, the sulfuric acid regenerant is delivered by a pump 41 from the regenerant reservoir 40 into the suppressor regenerant channel 36b to supply hydronium ions used in the suppression of ion chromatographic eluent (KOH). The effluent from channel 36b contains a mixture of potassium sulfate and sulfuric acid. The used regenerant liquid stream is then directed to the inlet of the ion reflux column in the electrolytic regenerant recycle device.

The construction of the electrolytic regenerant recycle device 56 of the embodiment illustrated in FIG. 6 is similar to the one used in the embodiment illustrated in FIG. 4. Device 56 serves the function of converting potassium sulfate in the suppressor effluent to sulfuric acid. The operation of device 56 in this embodiment is described below. Under the applied electrical field, potassium ions in the incoming regenerant solution migrate across the cation exchange connector 62b located near the inlet region of device 56 into the cathode compartment 62 and combine with hydroxide ions generated at the cathode 62a to form a potassium hydroxide solution. In the meantime, water is oxidized to form hydronium ions at the anode compartment 60 located near the outlet of the electrolytic regenerant recycle device 56. Hydronium ions migrate across the cation exchange connector 60 to the resin bed 26 of device 56 and combine with sulfate to form sulfuric acid. In this embodiment, the amount of current applied to device 56 should be adjusted to a level that is sufficient to ensure the complete removal of potassium ions in the regenerant stream to convert potassium sulfate to sulfuric acid. The sulfuric acid regenerant solution is then recycled back to the regenerant reservoir 40. The ion chromatography system illustrated in FIG. 6 provides another approach according to the invention to recycle the sulfuric acid regenerant used in the operation of the chemically-regenerated suppressor in an ion chromatography system.

It should be pointed out that, by using appropriate anion exchange materials, the various embodiments described above can also be implemented in forms that are suitable for suppressing acid eluents for determination of cationic analytes.

The following examples illustrate the present invention in ion chromatographic separation of ionic analytes

EXAMPLE 1

Ion Chromatography System Using Electrolytic Eluent Generation with Recycled Source Ions and Electrolytic Suppression with Recycled Regenerant Water.

This example demonstrates the use of an ion chromatography (IC) system using electrolytic eluent generation with recycled source ions and electrolytic suppression with recycled regenerant water in the separation of common anions. The IC system used in the experiment was constructed according to the scheme shown in FIG. 1. A modified Dionex P680 pump (Dionex Corporation, Sunnyvale, Calif.) was used to deliver deionized water at 10 µL/min. To generate and recycle a KOH eluent, deionized water was first passed through Dionex ATC-HC and CTC-1 columns to remove ionic contaminants and then routed into the KOH generation chamber of the KOH eluent generation and recycle module. The KOH eluent generation and recycle module was prepared by modifying a Dionex EGC-KOH cartridge (P/N 058900) through the addition of an ion reflux column placed in the potassium ion electrolyte reservoir which was filled with 1.0 liter of 0.5 M KOH. The ion reflux column was prepared by using a cylindrical PEEK housing that has cylindrical internal cavity of 9-mm ID×150 mm length which was packed with cation exchange resin in the hydronium form (8% cross-linked and 20 µm sulfonated styrene divinylbenzene resin beads, Dionex Corporation). The outlet of the column was fitted a flow-through Pt anode which was in direct physical contact with the cation exchange resin bed. The inlet region of the column was fitted with cation exchange connector that separated the resin bed from the potassium electrolyte solution in the ion source reservoir. A Dionex EG40 eluent generator control module was used to supply DC currents to the KOH eluent generation and recycle module.

The outlet of the KOH eluent generator was connected to a high-pressure degas unit to remove hydrogen gas generated during the electrolytic eluent generation process. A Rheodyne PEEK high-pressure injection valve (Cotati, Calif.) was used for injection of samples. The capillary anion separation column was prepared by packing a proprietary Dionex surface-functionalized anion exchange resin in a 1/16-inch OD PEEK tubing of 250 mm in length and 380 µm in internal diameter. A Dionex ED50A conductivity detector equipped with a modified flow-through conductivity cell was used. Dionex Chromeleon 6.6 chromatography data management computer workstation was used for instrument control, data collection, and processing.

In this example, an electrolytic capillary suppressor was prepared as described below. The capillary anion suppressor consisted of three PEEK chambers. The eluent chamber contained a cation exchange capillary tubing embedded tightly inside a bed (8 mm ID×10 mm in length) of cation exchange resin (8% cross-linked and 20-µm sulfonated styrene divinylbenzene resin beads, Dionex Corporation). Provisions were made provide separate fluid connections to the cation exchange capillary tubing in the resin bed. A 15-cm length of a proprietary grafted and sulfonated TFE capillary tubing of 0.004-inch ID×0.010-inch OD (Dionex Corporation) was used in the construction of the electrolytic capillary anion suppressor. The eluent chamber was physically separated from the cathodic regenerant chamber and anodic regenerant chamber using proprietary grafted and sulfonated TFE cation exchange ion exchange membranes (Dionex Corporation). The cathode chamber contained a perforated Pt cathode and the anode chamber contains a perforated Pt anode. Both electrode chambers had two liquid connecting ports (inlet and outlet). In this example, the suppressed eluent from the outlet of the conductivity cell was routed to waste.

A Dionex GS 50 pump was used to deliver the stream of regenerant water through a Dionex ATC HC column packed with anion exchange resin in the hydroxide form at 0.10 mL/min. The regenerant water was routed through the resin bed in eluent chamber, then to the anodic regenerant chamber and the cathodic regenerant chamber of the electrolytic anion suppressor. A Dionex RFC30 module was used to supply a DC current of 25 mA to the electrolytic anion suppressor. The catalytic gas elimination columns where hydrogen and oxygen gases react catalytically to form water were prepared by packing small strips of Pt foil in PEEK columns of 4-mm ID×50-mm length. One catalytic gas elimination column was placed downstream from the outlet of cathode chamber of the electrolytic suppressor. The other catalytic gas elimination column was placed downstream from the outlet of the ion reflux column. In one set of experiments, the KOH eluent generation and recycle module was programmed to generate and recycle 35 mM KOH at 10 µL/min by applying 0.563 mA of DC current to the device. The regenerant reservoir was initially filled with 100 mL of deionized water. The regenerant flow rate was 0.10 mL/min. The system was used to perform separation of five common anions (fluoride, chloride, nitrate, sulfate, and phosphate) continuously for more than 240 hours. No noticeable loss of regenerant water in the reservoir was observed over the period of 240 hours. If the regenerant water was not recycled, the consumption of regenerant water would have been 1440 mL.

Figure 7:
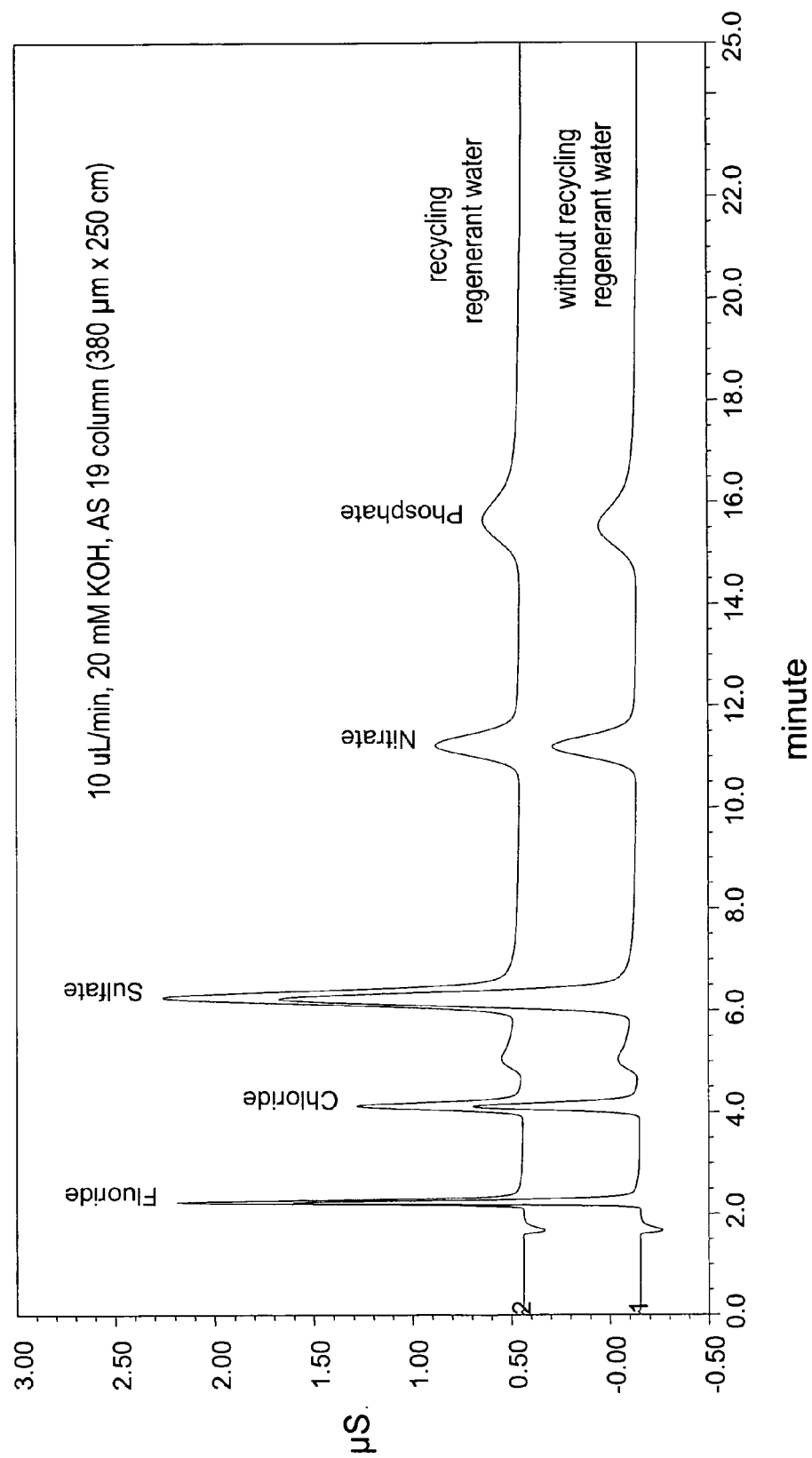
FIG. 7 is a chromatogram illustrating the present invention.

FIG. 7 shows the separation of five common anions obtained using the system shown in FIG. 1 by operating the electrolytic suppressor in the external water mode either with fresh regenerant water or with the recycled regenerant water.

Figure 8:
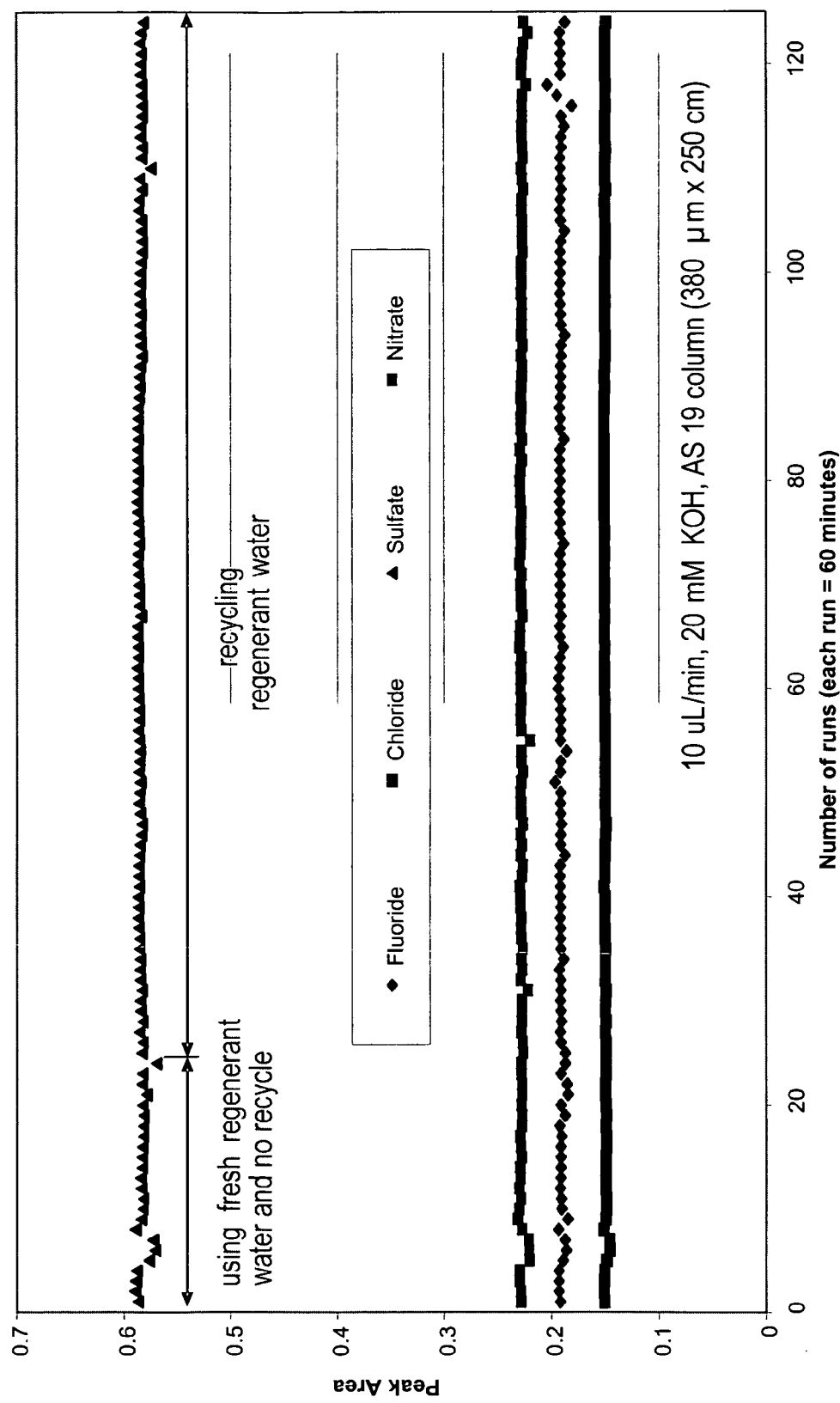
FIGS. 8 and 9 illustrate reproducibility data using the present invention.
Figure 9:
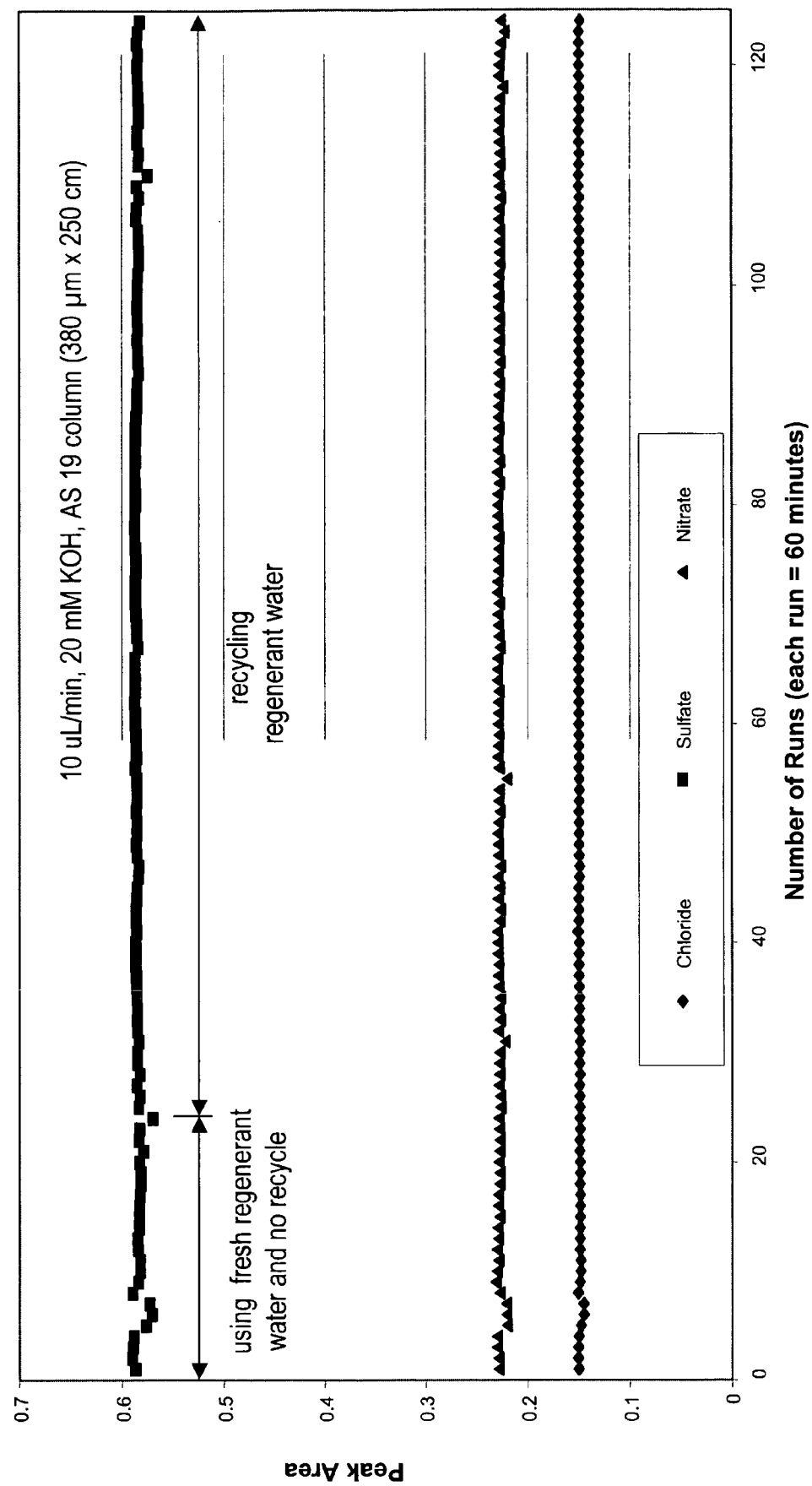

FIGS. 8 and 9 show the analyte retention time and peak area response reproducibility data obtained during the experiments. The results show that essentially identical separations were achieved under the conditions with or without recycling the regenerant water. For example, the average sulfate retention time was 6.25 minutes with a relative standard deviation (RDS) of 0.17 percent (n=24) and sulfate peak area response was 0.5822 µS minute with a RDS of 0.91 percent (n=24) using over a period of 24 hours when the electrolytic suppressor was operated in the external water mode with fresh regenerant water. When the electrolytic suppressor was operated in the external water mode with recycled regenerant water, the average sulfate retention time was 6.23 minutes with a RDS of 0.36 percent (n=100) and sulfate peak area response was 0.5850 µS minute with a RDS of 0.29 percent (n=100) using over a period of 100 hours.

Therefore, the above results demonstrate that the ion chromatography system using electrolytic eluent generation with recycled source ions and electrolytic suppression with recycled regenerant water can be used to provide reliable determination of target anionic analytes.

EXAMPLE 2

Ion Chromatography System Using Electrolytic Suppression with Recycled Regenerant Water.

This example demonstrates the use of an IC system using electrolytic suppression with recycled regenerant water in the separation of common anions. The IC system used in the experiment was constructed according to the embodiment shown in FIG. 3. A modified Dionex P680 pump (Dionex Corporation, Sunnyvale, Calif.) was used to deliver deionized water at 10 µL/min. To generate a KOH eluent, deionized water was first passed through Dionex ATC-HC and CTC-1 columns to remove ionic contaminants and then routed into the KOH generation chamber of a Dionex EGC-KOH eluent generator cartridge (P/N 058900). The outlet of the KOH eluent generator was connected to a high-pressure degas unit to remove hydrogen gas generated during the electrolytic eluent generation process. A Rheodyne PEEK high-pressure injection valve (Cotati, Calif.) was used for injection of samples. The capillary anion separation column was prepared by packing a proprietary Dionex surface-functionalized anion exchange resin in a 1/16-inch OD PEEK tubing of 250 mm in length and 380 µm in internal diameter. The electrolytic suppressor described in Example 1 was used. The suppressed eluent from the conductivity cell was routed to waste. A Dionex GS 50 pump was used to deliver the stream of regenerant water through a Dionex ATC HC column packed with anion exchange resin in the hydroxide form at 0.10 mL/min. A Dionex RFC30 module was used to supply a DC current of 25 mA to the electrolytic anion suppressor. A Dionex ED50A conductivity detector equipped with a modified flow-through conductivity cell was used. A Dionex Chromeleon 6.6 chromatography data management computer workstation was used for instrument control, data collection, and processing.

The electrolytic regenerant recycle device was constructed by immersing an ion reflux column in a 100-mL reservoir filled with 0.5 M KOH solution. A Pt cathode was placed in the electrolyte reservoir of the electrolytic regenerant recycle device. The ion reflux column was prepared by using a cylindrical PEEK housing that has cylindrical internal cavity of 9-mm ID×150 mm length which was packed with cation exchange resin in the hydronium form. The outlet of the column was fitted a flow-through Pt anode which was in direct physical contact with the cation exchange resin bed. The inlet region of the column was fitted with cation exchange connector that separated the resin bed from the potassium electrolyte solution in the ion source reservoir. A Dionex SC20 control module was used to supply 2.0 mA of DC current to the electrolytic regenerant recycle device. One catalytic gas elimination column (4-mm ID×50-mm length) prepared by packing small strips of Pt foil was placed downstream from the outlet of cathode chamber of the electrolytic suppressor to allow the reaction of hydrogen and oxygen catalytically to form water.

In one set of experiments, the regenerant reservoir was initially filled with 100 mL of deionized water. The system was used to perform the separation of five common anions (fluoride, chloride, nitrate, sulfate, and phosphate) using 35 mM KOH at 10 µL/min continuously for 45 hours. No noticeable loss of regenerant water was observed over the period of 45 hours. If the regenerant water was not recycled, the consumption of water would have been 270 mL. The results show that identical separations were achieved under the conditions with or without recycling the regenerant water. During the period of 45 hours, the percent RDS of analyte retention time were 0.34% for chloride and 0.58% for sulfate (n=45); the percent RDS of analyte peak height response were 0.70% for fluoride and 0.69% for sulfate (n=45). Therefore, the above results demonstrate that the ion chromatography system with the recycled regenerant water shown in FIG. 3 can be used to provide reliable determination of target anionic analytes.

EXAMPLE 3

Ion Chromatography System Using Electrolytic Suppression with Recycled Regenerant Water.

This example demonstrates the use of an IC system using electrolytic suppression with recycled regenerant water in the separation of common anions. The IC system used in the experiment was constructed according to the embodiment shown in FIG. 4. A modified Dionex P680 pump (Dionex Corporation, Sunnyvale, Calif.) was used to deliver deionized water at 10 µL/min. To generate a KOH eluent, deionized water was first passed through Dionex ATC-HC and CTC-1 columns to remove ionic contaminants and then routed into the KOH generation chamber of a Dionex EGC-KOH eluent generator cartridge (P/N 058900). The outlet of the KOH eluent generator was connected to a high-pressure degas unit to remove hydrogen gas generated during the electrolytic eluent generation process. A Rheodyne PEEK high-pressure injection valve (Cotati, Calif.) was used for injection of samples. The capillary anion separation column was prepared by packing a proprietary Dionex surface-functionalized anion exchange resin in a 1/16-inch OD PEEK tubing of 250 mm in length and 380 μm in internal diameter. The electrolytic suppressor described in Example 1 was used. The suppressed eluent from the conductivity cell was routed to the anode and cathode compartments of the electrolytic regenerant device before going to waste. A Dionex GS 50 pump was used to deliver the stream of regenerant water through a Dionex ATC HC column packed with anion exchange resin in the hydroxide form at 0.10 mL/min. A Dionex RFC30 module was used to supply a DC current of 25 mA to the electrolytic anion suppressor. A Dionex ED50A conductivity detector equipped with a modified flow-through conductivity cell was used. A Dionex Chromeleon 6.6 chromatography data management computer workstation was used for instrument control, data collection, and processing.

In this example, a Dionex anion Atlas electrolytic suppressor (P/N 056116) was used as the electrolytic regenerant recycle device. A Dionex SC20 module was used to supply 5 mA of DC current to the electrolytic regenerant recycle device. One catalytic gas elimination column (4-mm ID×50-mm length) prepared by packing small strips of Pt foil was placed downstream from the outlet of cathode chamber of the electrolytic suppressor to allow the reaction of hydrogen and oxygen catalytically to form water. The effluent from the outlet of the catalytic gas elimination column was directed to the ELUENT IN port of the anion Atlas electrolytic suppressor. The effluent from the ELUENT OUT port of the anion Atlas electrolytic suppressor was recycled back to the regenerant reservoir.

In one set of experiments, the regenerant reservoir was initially filled with 100 mL of deionized water. The system was used to perform the separation of five common anions (fluoride, chloride, nitrate, sulfate, and phosphate) using 35 mM KOH at 10 μL/min continuously for 95 hours. No noticeable loss of regenerant water was observed over the period of 95 hours. If the regenerant water was not recycled, the consumption of water would have been 570 mL. During the period of 95 hours, the percent RDS of analyte retention time were 0.11% for chloride and 0.17% for sulfate (n=95); the percent RDS of analyte peak area response were 0.71% for chloride and 0.74% for sulfate (n=95). Therefore, the above results demonstrate that the ion chromatography system with the recycled regenerant water shown in FIG. 4 can be used to provide reliable determination of target anionic analytes.

EXAMPLE 4

Ion Chromatography System Using Chemically-regenerated Suppressor with Recycled Sulfuric Acid Regenerant This example demonstrates the use of an IC system using chemically-regenerated suppressor with recycled sulfuric acid regenerant in the separation of common anions. The IC system used in the experiment was constructed according to the embodiment shown in FIG. 6. A modified Dionex P680 pump (Dionex Corporation, Sunnyvale, Calif.) was used to deliver deionized water at 10 μL/min. To generate a KOH eluent, deionized water was first passed through Dionex ATC-HC and CTC-1 columns to remove ionic contaminants and then routed into the KOH generation chamber of a Dionex EGC-KOH cartridge (P/N 058900). The outlet of the KOH eluent generator was connected to a high-pressure degas unit to remove hydrogen gas generated during the electrolytic eluent generation process. A Rheodyne PEEK high-pressure injection valve (Cotati, Calif.) was used for injection of samples. The capillary anion separation column was prepared by packing a proprietary Dionex surface-functionalized anion exchange resin in a 1/16-inch OD PEEK tubing of 250 mm in length and 380 μm in internal diameter.

In this example, the anion suppressor described in Example 1 was used in the chemical regeneration mode using sulfuric acid as the regenerant. A Dionex GS 50 pump was used to deliver the stream of 20 mM sulfuric acid to the resin bed in the eluent chamber of the suppressor at 0.10 mL/min. A Dionex ED50A conductivity detector equipped with a modified flow-through conductivity cell was used. A Dionex Chromeleon 6.6 chromatography data management computer workstation was used for instrument control, data collection, and processing.

In this example, a Dionex anion Atlas electrolytic suppressor (P/N 056116) was used as the electrolytic regenerant recycle device. A Dionex RFC-30 control module was used to supply 5 mA of DC current to the electrolytic regenerant recycle device. The effluent from the outlet of anion suppressor was directed to the ELUENT IN port of the anion Atlas electrolytic suppressor. The effluent from the ELUENT OUT port of the anion Atlas electrolytic suppressor was recycled back to the regenerant reservoir.

In one set of experiments, the regenerant reservoir was initially filled with 125 ml of 20 mM sulfuric acid. The system was used to perform the separation of five common anions (fluoride, chloride, nitrate, sulfate, and phosphate) using 35 mM KOH at 10 μL/min continuously for more than 170 hours. No noticeable loss of sulfuric acid regenerant was observed over the period of 170 hours. If the sulfuric acid regenerant was not recycled, the consumption of 20 mM sulfuric acid would have been 1020 mL. During the period of 170 hours, the percent RDS of analyte retention time were 0.10% for chloride and 0.17% for sulfate (n=170); the percent RDS of analyte peak area response were 1.18% for chloride and 1.72% for sulfate (n=170). Therefore, the above results demonstrate that the ion chromatography system with the recycled sulfuric acid regenerant shown in FIG. 6 can be used to provide reliable determination of target anionic analytes.

What is claimed is:

1. Suppressed ion chromatographic apparatus using a regenerant recycle loop, comprising
  (a) an ion separation device including ion separation medium with exchangeable ions of one charge, positive or negative,
  (b) a membrane suppressor comprising a sample stream flow channel, having an inlet and an outlet, a regenerant flow channel, having an inlet and an outlet, and an ion exchange membrane separating said sample stream flow channel and regenerant flow channel,
  (c) a detector having an inlet and an outlet, said detector inlet being in fluid communication with said sample stream flow channel outlet,
  (d) a container for regenerant solution,
  (e) a first conduit providing fluid communication between said ion separation device and said sample stream flow channel inlet,
  (f) a second conduit providing fluid communication between said regenerant solution container and said regenerant flow channel, (g) a third conduit providing fluid communication between said regenerant channel and said regenerant solution container, and (h) a regenerant solution recycle loop comprising said second and third conduits, said recycle loop being out of fluid communication with said detector outlet.

2. The apparatus of claim 1 in which said recycle loop is isolated from a liquid flow path through said sample stream flow channel and said detector.

3. The apparatus of claim 1 further comprising (i) an ion removal device comprising ion exchange medium in said recycle loop and a first electrode out of the path of regenerant liquid in said loop.

4. The apparatus of claim 3 in which said ion removal device further comprises (j) a first ion exchange barrier to bulk liquid flow separating said ion removal device ion exchange medium from said first electrode.

5. The apparatus of claim 4 in which said detector outlet is in fluid communication with said first electrode.

6. The apparatus of claim 4 in which said ion removal device forms part of an electrolytic generator which further comprises (k) a second electrode spaced apart from said first electrode, and (l) a second ion exchange barrier to bulk liquid flow, disposed between said first and second electrodes, said second electrode being in fluid communication with said ion separation device.

7. The apparatus of claim 4 further comprising (i) an aqueous liquid source, and (j) a first pump for pumping aqueous liquid from said aqueous liquid source past said second electrode.

8. The apparatus of claim 1 further comprising (i) a catalytic gas elimination device disposed along said second conduit and in fluid communication therewith.

9. The apparatus of claim 1 further comprising (i) a first pump for pumping liquid though said recycle loop.

10. The apparatus of claim 9 further comprising a second pump for pumping a liquid sample stream through said ion separation device, suppressor and detector.

11. The apparatus of claim 1 in which said ion separation device comprising a chromatography column.

* * * * *

UNITED STATES PATENT AND TRADEMARK OFFICE
CERTIFICATE OF CORRECTION

PATENT NO. : 7,473,354 B2 Page 1 of 1
APPLICATION NO. : 11/229022
DATED : January 6, 2009
INVENTOR(S) : Yan Liu et al.

It is certified that error appears in the above-identified patent and that said Letters Patent is hereby corrected as shown below:

In Col. 5, lines 57 and 58, change "(2 $H_2O+2e^- \rightarrow 2OH^{31} +H_2\uparrow$)" to --(2 $H_2O+2e^- \rightarrow 2OH^- +H_2\uparrow$)--.

Signed and Sealed this

Twenty-third Day of November, 2010

David J. Kappos
*Director of the United States Patent and Trademark Office*